United States Patent
Wurzinger et al.

(10) Patent No.: US 8,490,415 B2
(45) Date of Patent: Jul. 23, 2013

(54) SPECIMEN HOLDER FOR A HIGH-PRESSURE FREEZING DEVICE

(75) Inventors: Paul Wurzinger, Deutsch-Wagram (AT); Johannes Leunissen, Dunedin (NZ)

(73) Assignee: Leica Mikrosysteme GmbH, Vienna (AT)

( * ) Notice: Subject to any disclaimer, the term of this patent is extended or adjusted under 35 U.S.C. 154(b) by 379 days.

(21) Appl. No.: 12/826,735

(22) Filed: Jun. 30, 2010

(65) Prior Publication Data

US 2011/0000230 A1   Jan. 6, 2011

(30) Foreign Application Priority Data

Jul. 1, 2009   (AT) .................. A 1026/2009

(51) Int. Cl.
    *F25D 25/00*   (2006.01)
(52) U.S. Cl.
    USPC .................................. 62/62; 62/78
(58) Field of Classification Search
    USPC ... 62/62, 64, 78, 45.1, 51.1; 220/500; 435/1.3
    See application file for complete search history.

(56) References Cited

U.S. PATENT DOCUMENTS

| | | | | |
|---|---|---|---|---|
| 4,314,459 | A | * | 2/1982 | Rivoire ................ 62/51.1 |
| 5,195,325 | A | * | 3/1993 | Short et al. ............ 62/50.2 |
| 7,939,316 | B2 | * | 5/2011 | Woods et al. .......... 435/307.1 |
| 2005/0188705 | A1 | * | 9/2005 | Jones et al. ............... 62/86 |
| 2008/0003561 | A1 | * | 1/2008 | Woods et al. ........... 435/1.3 |
| 2009/0011505 | A1 | | 1/2009 | Leunissen |

FOREIGN PATENT DOCUMENTS

| | | |
|---|---|---|
| DE | 10261625 A1 | 7/2004 |
| WO | 97/26198 A1 | 7/1997 |
| WO | 2007/120829 A2 | 10/2007 |

OTHER PUBLICATIONS

Austrian Patent Office—Office Action dated Nov. 11, 2009 in Austrian Patent Application No. 1026/2009.

* cited by examiner

*Primary Examiner* — Mohammad M Ali
(74) *Attorney, Agent, or Firm* — Hodgson Russ LLP

(57) ABSTRACT

A method for preparing a hydrous, cryopreserved sample that is enclosed in a sample container (1, 1*a*, 1*b*, 1*c*), in the case of which, at least sample material is introduced into the sample container; this is then sealed pressure-tight and subsequently cooled by a cryogen (8) in a temporal and spatial sequence, a sacrificial region (4) of the container contents (2) initially solidifying and, only subsequently thereto, the entire container contents solidifying. A sample container (1*a*) that may be preferably used in this case is designed to be tubular, sealed at both ends thereof, and to essentially have a U-shaped form.

17 Claims, 1 Drawing Sheet

SPECIMEN HOLDER FOR A HIGH-PRESSURE FREEZING DEVICE

CROSS REFERENCE TO RELATED APPLICATIONS

Figure 1:
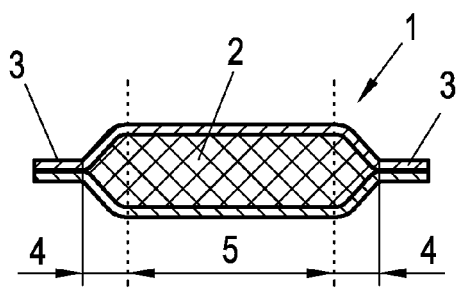

This application claims priority of the Austrian patent application number 1026/2009 filed Jul. 1, 2009, the entire disclosure of which is incorporated by reference herein.

FIELD OF THE INVENTION

The present invention relates to a method for preparing a hydrous, cryopreserved sample that is enclosed in a sample container, in the case of which, at least sample material is introduced into the sample container; this sample container is then sealed pressure-tight and subsequently cooled by a cryogen.

The present invention also relates to a sample container for implementing the method.

BACKGROUND OF THE INVENTION

A method as well as a device of this kind are already known from the Austrian Patent Application AT 505427 A1 of the Applicant. This document discusses approaches used when working with biological samples to freeze the specimen under high pressure conditions, liquid nitrogen being used as a cryogen, for example. Since the samples are hydrous, enclosing the sample during cooling and preventing its expansion results in a considerable pressure due to the expansion of the water when it freezes into ice. As the document explains in detail, this pressure is desired since it permits a high-pressure freezing without entailing substantial outlay for equipment and without requiring substantial cooling agent consumption. It is an aim of the known method for the water in the sample to pass through a glass formation or at least a microcrystal formation—in contrast to the samples that are frozen at atmospheric pressure or also to shock-frozen samples. To achieve better thermal conditions for the freezing process, the sample container can also be precooled before the actual freezing process, for example, in an ethanol or ethanol/methanol mixture whose temperature is adjusted to between 273 and 251 K. The preferred value is just above the triple point temperature of water-ice Ih-ice III (251K). When the sample is in thermal equilibrium, a cryogen is then used to carry out the actual freezing process.

Following the freezing process, the sample containers are opened or cut; the sample is removed and then submitted to a further treatment, for example, a cryo-substitution at temperatures of typically above 183K, for example, of minus 80° C. to −40° C. using acetone. On the other hand, the samples can also be slit or cut using a microtome of a known type.

Even though the method discussed in the above mentioned document offers a substantial improvement in the field of cryopreservation of biological samples, it turns out that, in the case of sample tubes whose ends are pinched closed, for example, the ends can become pervious at the high pressures of over 2000 bar that arise, making the sample unusable. On the other hand, usable, i.e., vitreous/microcrystalline frozen sample regions are often present in the middle of sample regions that exhibit large crystals of hexagonal ice I and, therefore, are unusable. Generally, it cannot be predicted which sample regions will be usable and which will be unusable.

Experience shows that the rate of this permeability can be reduced when the entire sample is preferably cooled as simultaneously as possible. To this end, the sample tube is oriented in parallel to the surface of the cryogen, for example, during immersion. In this case, however, usable, i.e., vitreous/microcrystalline frozen sample regions are often present in the middle of sample regions that exhibit large crystals of hexagonal ice I and are, therefore, unusable. Generally, one cannot predict which sample regions will be usable and which will be unusable.

SUMMARY OF THE INVENTION

It is, therefore, an object of the present invention to improve the known method, respectively the known devices for implementing the method in a way that will allow the pressure to be reliably maintained during the freezing process and defined, usable regions of the sample to be obtained.

The mentioned objective is achieved by a method of the type mentioned at the outset, which provides for the container to be cooled in a temporal and spatial sequence in accordance with the present invention, a sacrificial region of the container contents initially solidifying and, only subsequently thereto, the container contents also solidifying.

Thus, the fundamental idea of the present invention is not to cool the sample container containing the sample as quickly as possible by completely immersing or plunging it into a cryogen such as liquid nitrogen, for example, but rather to initially cool regions of the container where a mostly unused "sacrificial region" of the container contents solidifies, and, only then, to allow further solidification of the entire container contents to occur.

It may be expedient, prior to the sealing and cooling process, for the sacrificial region of the container to be filled with a substance that expands during solidification. The solidification of the sacrificial region then leads to an increase in pressure in the initially still unsolidified sample portions, thereby preventing disturbing crystals from forming during the final solidification of the sample. In this context, this substance may advantageously be at least partially composed of water.

One favorable variant, which is also suited for small sample amounts, provides for a tubular sample container, which is sealed at both ends thereof, to initially be cooled at least one end by a cryogen. However, in this variant, the sealing of the end that has initially not been cooled, presents a technical challenge that may be elegantly met by the specific embodiments described in the following.

One expedient option for a temporally and spatially controlled cooling provides for using a cryogen to cool a tubular sample container that is sealed at both ends thereof and has a means in a region between the ends thereof that ensures a reduced coupling to the ambient environment in terms of thermal conductivity. In this context, the means may be an insulation that is externally affixed to the container.

A simply designed sample container for implementing the method is distinguished by a tubular form, a sealed configuration at both ends, and essentially a U-shaped form.

Another useful variant of the sample container may provide for it to be tubular, sealed at both ends thereof, and provided with an insulation in a region between the ends thereof.

An insulation in the useful region is also simple to implement when at least one portion of a holding device that engages on the container is designed as insulation.

In some cases, it may also be advantageous when the sample container is composed of two mutually separable parts.

In this case, to connect the parts, it may be provided that the two parts be able to be sealingly screwed together.

To eliminate the need for a screw-coupling that may possibly be painstaking to implement, particularly when working with small containers, the two parts may also be able to be pressed together in a clamping device.

BRIEF DESCRIPTION OF THE DRAWING VIEWS

Figure 2:
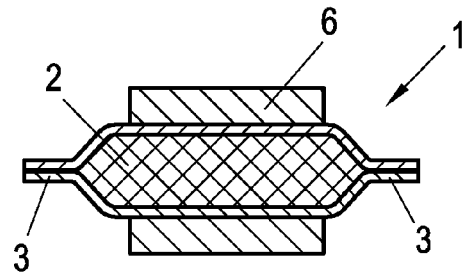
Figure 3:
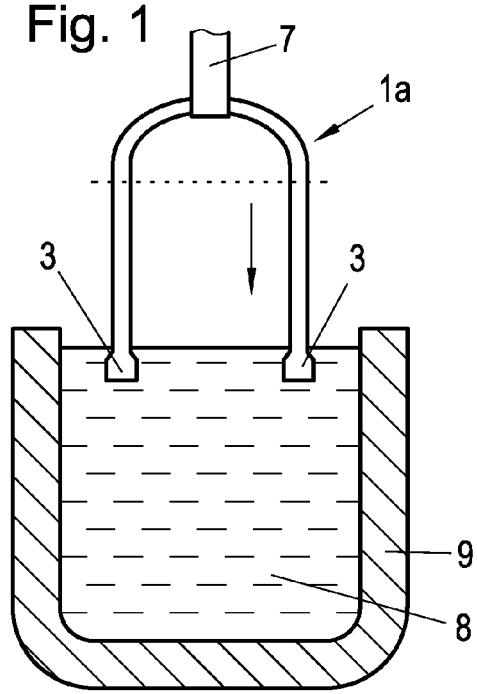
Figure 4:
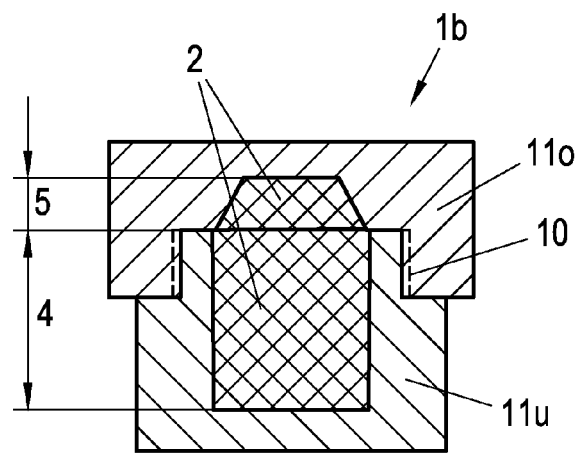
Figure 5:
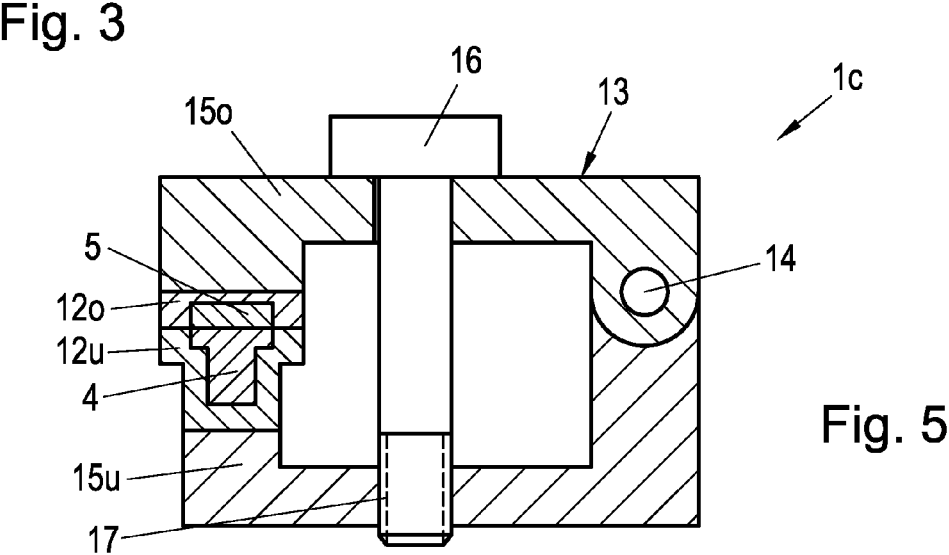

The present invention, together with further advantages thereof, is clarified in greater detail in the following with reference to exemplary specific embodiments that are illustrated in the drawing, whose figures show:

FIG. 1: a sample tube that is pinched closed at both ends, having a sample material enclosed therein;

FIG. 2: a sample tube as in accordance with FIG. 1, however, surrounded by an insulation on the exterior thereof;

FIG. 3: a U-shaped sample tube during immersion into a cryogen;

FIG. 4: a two-part screw-couplable sample container having a relatively large sacrificial region in one portion and the actual sample material in the other portion; and FIG. 5: likewise, a two-part container that is clamped into a clamping device.

DETAILED DESCRIPTION OF THE INVENTION

FIG. 1 shows a tubular sample container 1, which may be used for single cells or small organisms such as nematodes, for example, and is formed from a capillary tube. At an outside diameter of 0.6 mm and an inside diameter of 0.3 mm, an exemplary specific embodiment of such a sample container is 16 mm long, for example. Once the sample container is filled with a hydrous biological sample, which then forms container contents 2, the container made of copper, for example, is firmly sealed at ends 3 thereof, for example, pinched over a length of approximately 1 mm, using pliers Subsequently thereto, the container is initially cooled at both ends 3 thereof, and the remainder of the container is then cooled, so that the entire container contents solidify. It is clear that there are no clear transitions here due to the thermal conductivity of the container wall. However, in the present case, particularly when working with a tubular container 1 having pinched ends, the advantage is attained that the container contents first solidify in the end regions of the tube. Due to the early solidification of the end regions, the container ends will no longer burst open since they are protected by the solidified sample material. At the same time, the solidification of the sample ends, which in this case are used as sacrificial regions, brings about the desired pressure buildup.

That region (or those regions) of the container contents which solidifies/solidify first and which does/do not necessarily need to contain sample material, as will be clarified further below, is/are referred to as "sacrificial region(s)" in the context of the present invention, since such regions are generally not used for obtaining samples. In the case of a container in accordance with FIG. 1, following the complete freezing of container contents 2, for example, the two end regions of the container are cut away at the locations indicated by dotted lines, thereby yielding two sacrificial regions 4 and one useful region 5. The useful region contains that sample material which is used further in the known manner already explained above.

There are different approaches, respectively container designs that lend themselves to the practical implementation of the method according to the present invention. For example, to allow the freezing to commence first at the ends, the method may be refined in such a way that a tubular sample container, which is sealed at both ends thereof, has a means in a region between the ends thereof that ensures a reduced coupling to the ambient environment in terms of thermal conductivity.

Thus, FIG. 2 shows a container as illustrated in FIG. 1, however, having an insulation 6 that is affixed to its outer wall and is made of a suitable material, for example, plastic. Such a filled container, as in accordance with FIG. 1, may then be immersed as a whole in a cryogen; due to the insulation, useful region 5 not solidifying until after sacrificial regions 4.

In accordance with another option for implementing the spatially and temporally controlled cooling, different wall thicknesses of the sample container may be provided, i.e., a greater wall thickness may be selected around the useful region than around a sacrificial region. It is particularly advantageous that a container material having a low thermal conductivity be used to realize this specific embodiment.

A container form is readily apparent in FIG. 3 that facilitates the implementation of the method according to the present invention in a simple, but effective manner. In this case, a sample container 1a is tubular and essentially configured in a U-shape. As in the case of the designs according to FIGS. 1 and 2, the ends are pinched closed, it being self-evident here that the ends may also be sealed in different ways, for example, by using suitably formed conical plugs, for example. For the freezing process, container 1a, which is held at its bent base portion by a holding device 7, for example, is dipped into a Dewar vessel 9 filled with liquid nitrogen, for example, and, in fact, as illustrated, initially just the two end regions 3 thereof and, only subsequently thereto, is it (the container) completely immersed. In the end regions, container contents 2 naturally freeze, respectively solidify first, whereby the sealing points are sealed, and the pressure buildup cannot result in the container contents escaping.

It is noted in connection with holding device 7 shown in FIG. 3 that a part of such a holding device that grips around the container may also be used as insulation in the sense of insulation 6 in accordance with FIG. 2.

The containers used within the scope of the present invention need not have a tubular nor one-piece design, as will be clarified in the following with reference to two further specific embodiments.

FIG. 4 shows a container 1b which is composed of two parts 11o, 11u having a thread 10 that are able to be sealingly screwed together. Each of the two container parts 11o, 11u has an interior space; in the case of the illustrated example, the lower container part 11a in the drawing having a larger volume than upper part 11o. A variant of the method according to the present invention, in which container contents 2 are not homogeneously composed of sample material, is explained with reference to the example according to FIG. 4. Rather, a sacrificial region 4, in this case the interior space of lower container part 11u, is filled with a substance that significantly expands upon solidification, particularly when working with a substance that is at least partially composed of water or when working with pure water. On the other hand, the actual sample material is contained in the comparatively smaller interior space of top container part 11o, i.e., useful region 5. A variant of this kind ensures that the necessary pressure buildup is provided even when either only little sample material is available or the sample material itself is not able to build up sufficient pressure due to its properties. The cooling of a container in accordance with FIG. 4 may be spatially and temporally controlled in accordance with the present invention in such a way that part 11u thereof, which contains sacrificial region 4—and, in this case the water or the like—is first dipped into a cryogen and, only subsequently thereto, is it (the container) completely immersed. The water that initially expands during solidification or another suitable substance thereby exerts the desired pressure on the actual sample material already before the solidification thereof, thereby enabling it to obtain the desired structure referred to at the outset.

With respect to variations of a two-part container, it may also be provided for the entire interior space to be configured in one of the two container parts and for the other container part to merely constitute a lid.

FIG. 5 depicts a likewise two-part container 1c whose two parts 12o, 12u, however, are not screwed together, but merely placed one on the other. To ensure a sealing of the entire container contents, which is composed of an upper useful region 5 and a lower sacrificial region 4, even in the case of a pressure buildup in the interior of the container, the container is clamped in a clamping device. In principle, such a clamping device 13 may have any given design, in the example in accordance with FIG. 5, two arms 15o, 15u that are pivotable about a pivot pin 14 being provided, which, by the free ends thereof, press the two container parts 12o, 12u sealingly against each other via a clamping screw 16 that cooperates via a thread 17 with arm 15u, which is the lower arm in the drawing.

In terms of sacrificial region 4 and useful region 5, container 1c according to FIG. 5 is apportioned similarly to container 1b according to FIG. 4. Also, the cooling process is carried out analogously to the description provided in connection with FIG. 4.

LIST OF REFERENCE NUMERALS 1 also 1a, 1b, 1c, container
2 container contents
3 ends
4 sacrificial region
5 useful region
6 insulation
7 holding device
8 cryogen
9 Dewar vessel
10 thread
11o container part
11u container part
12o container part
12u container part
13 clamping device
14 pivot pin
15o arm
15u arm
16 clamping screw
17 thread

What is claimed is:

1. A method for preparing a hydrous, cryopreserved sample enclosed in a sample container comprising the steps of:
   introducing sample material into the sample container;
   sealing the sample container pressure-tight;
   cooling the sealed sample container in a cryogen in a temporal and spatial sequence, wherein contents in a sacrificial region of the sample container are solidified initially and, only subsequently thereto, remaining contents in the sample container are solidified;
   wherein the contents in the sacrificial region are mostly unused for obtaining samples.

2. The method as recited in claim 1, further comprising the step of filling the sacrificial region of the container with a substance that expands during solidification, wherein the step of filling is performed prior to the steps of sealing and cooling.

3. The method as recited in claim 2, wherein the substance is at least partially composed of water.

4. The method as recited in claim 1, wherein the sample container is a tubular sample container which is sealed at both ends thereof, and the tubular sample container is initially cooled at least one of the ends by the cryogen.

5. The method as recited in claim 1, wherein the sample container is a tubular sample container which is sealed at both ends thereof, and the tubular sample container has means in a region between the ends thereof for reducing thermal conductivity with the ambient environment.

6. The method as recited in claim 5, wherein the means includes insulation externally affixed to the container.

7. The method as recited in claim 1, further comprising the step of providing a U-shaped tubular container as the sample container.

8. The method as recited in claim 6, further comprising the step of providing the sample container.

9. The method as recited in claim 1, further comprising the step of providing a tubular container composed of two mutually separable parts as the sample container.

10. The method as recited in claim 9, wherein the two parts of the sample container are adapted to be sealingly screwed together.

11. The method as recited in claim 9, wherein the two parts of the sample container are adapted to be pressed together in a clamping device.

12. A system for preparing a hydrous, cryopreserved sample comprising:
   a tubular sample container including a sacrificial interior region and a useful interior region;
   a substance that expands during solidification received in the sacrificial interior region of the sample container; and
   a sample material received in the useful interior region of the sample container;
   wherein the contents in the sacrificial interior region are mostly unused for obtaining samples.

13. The system as recited in claim 12, wherein the sample container is composed of two mutually separable parts, wherein one of the two parts defines the sacrificial interior region and another of the two parts defines the useful interior region.

14. The system as recited in claim 13, wherein the volume of the sacrificial interior region is greater than the volume of the useful interior region.

15. The system as recited in claim 12, wherein the two parts of the sample container are adapted to be sealingly screwed together.

16. The system as recited in claim 12, wherein the two parts of the sample container are adapted to be pressed together in a clamping device.

17. An apparatus for preparing a hydrous, cryopreserved sample comprising:
   a U-shaped tubular sample container having a pair of opposite ends adapted to be sealed and a base portion between the opposite ends; and
   a holding device adapted to engage the base portion of the sample container while the sample container is cooled in a cryogen, wherein a portion of the holding device that engages the base portion is embodied as thermal insulation.

* * * * *